United States Patent [19]

Miller et al.

[11] Patent Number: 5,528,050
[45] Date of Patent: Jun. 18, 1996

[54] COMPACT SCAN HEAD WITH MULTIPLE SCANNING MODALITIES

[75] Inventors: Michael F. Miller, Mountain View; Lars Majlof, Saratoga; Robert C. Kain, San Jose, all of Calif.

[73] Assignee: Molecular Dynamics, Inc., Sunnyvale, Calif.

[21] Appl. No.: 508,342

[22] Filed: Jul. 24, 1995

[51] Int. Cl.$^6$ .................................................. G03B 42/00
[52] U.S. Cl. .................. 250/585; 250/586; 250/958.1
[58] Field of Search ............................. 250/585, 586, 250/458.1, 459.1, 461.1

[56] References Cited

U.S. PATENT DOCUMENTS

| | | | |
|---|---|---|---|
| 4,019,060 | 4/1977 | Woodman | 250/458.1 |
| 5,202,744 | 4/1993 | Louis | 356/73 |
| 5,304,810 | 4/1994 | Amos | 250/458.1 |
| 5,325,381 | 6/1994 | Paoli | 372/24 |
| 5,325,383 | 6/1994 | Davis et al. | 372/26 |
| 5,337,139 | 8/1994 | Shirasawa | 356/73 |
| 5,343,224 | 8/1994 | Paoli | 346/108 |

*Primary Examiner*—Davis L. Willis
*Assistant Examiner*—Kiet T. Nguyen
*Attorney, Agent, or Firm*—Schneck & McHugh

[57] ABSTRACT

A compact, movable scan head having multiple scanning modalities and capable of high speed, high resolution scanning of a variety of samples is disclosed. Stimulation and detection of storage phosphor screens and fluorescent samples are preferably achieved with a first and second channel in the optical path of the first side of the scan head. This first side preferably has a laser diode light source. Reading of reflective and transmissive signals is also possible. A third channel is available in the optical path of the second side of the scan head. This third channel preferably provides LED point scanning and reading of fluorescence, reflective, and transmissive signals received from the sample. The various modalities of the scan head of the present invention may or may not have coincident optical paths. Any two of the above channels, or additional channels similar to the above channels, may be incorporated into the scan head.

49 Claims, 7 Drawing Sheets

COMPACT SCAN HEAD WITH MULTIPLE SCANNING MODALITIES

TECHNICAL FIELD

This invention relates to moving head optical scanners for stimulation of a target sample and for reading the return signal radiation from the target.

BACKGROUND ART

Optical scanners for stimulation of target samples and for detection of the resulting signal radiation emerging from the samples are used in many experimental formats. Optical scanners having movable scan heads are particularly useful for variable field size. However, many existing scanners, including those with movable scan heads, are limited with respect to scan speed because of their numerous components and the high mass of their optical assemblies. It is desirable to increase scan speed without compromising resolution in order to scan many samples in a short period of time.

A wide variety of scan formats is necessary for many research and diagnostic applications. For example, emerging formats include the scanning of large gels containing fluorescent labels, and the scanning of miniature chips or membranes supporting minute samples. In addition to the variability desired with respect to scan formats, versatility with respect to types of optical analysis is extremely important. Analysis of samples based on storage phosphor emission, fluorescent, reflected, and transmitted light may be necessary. Space and cost considerations dictate the use of instruments allowing analysis in more than one of these modalities.

Because these various optical scanning modalities generally require exciting or stimulating light of a unique wavelength and collection and detection optics capable of separating the various types of returned signals from the target sample, merging many scanning modalities into one optical scanner has been difficult in the past. Providing multiple simultaneous incident wavelengths and subsequently descanning and detecting the coincident sample emission generally results in complex and expensive instruments and difficult analysis. For example, see U.S. Pat. No. 5,304,810 to Amos.

It is therefore an object of the present invention to provide a compact, versatile optical scanner of simple, lightweight, and low cost design for rapid scanning of target samples according to any of a multiple of scanning modalities.

DISCLOSURE OF THE INVENTION

The above object has been achieved with a movable compact scan head having multiple scanning modalities. The scan head supports two or more optical systems within a small space. The optical systems may or may not be coincident, each one designed for a specific stimulation and detection modality. Possible modalities include stimulation and detection of storage phosphor emission, fluorescence including chemi-fluorescence, reflection, and transmission. One optical system may include a laser diode or other compact lightweight laser device light source, and have a first channel for storage phosphor emission and a second channel for fluorescence. A separate optical system may have a light emitting diode (LED) light source and a third channel for reflection signals or fluorescence emission by a sample stimulated at a wavelength other than that of the second channel. Multiple combinations of light sources of various properties may be employed.

As used here, "laser diode" includes other compact, lightweight laser devices, The term "remotely positioned" means the element is not situated on the scan head. The term "wavelength" may signify a wavelength band, especially with regard to sample emission. The term "emission" includes storage phosphor, fluorescent, reflected, and transmitted signals from the sample.

Typically, a first side of the scan head supports a laser diode light source for stimulation of a sample at a first wavelength. Light emitted from the sample at both lower and higher wavelengths than the stimulating wavelength may be collected. This is possible through an interference-type spectral beam splitter which passes the laser diode wavelength and which reflects light below and above this wavelength toward the detection optics. For example, a red laser diode provides an excitation wavelength of approximately 635 nm. Storage phosphor emission resulting from this stimulation is generally at 390 nm and fluorescence emission is generally at 650 nm or more. Thus, these two types of signals from the sample or samples will be reflected by the beam splitter. An adjustable filter changer assembly providing the filters needed for isolating the signals of interest may be used in the detection path on this first side of the scan head. At least one filter is generally dedicated to passing light of a lower wavelength than the stimulating wavelength and at least one filter is generally dedicated to passing light of a higher wavelength than the stimulating wavelength. A detector, mounted on the scan head directly, or in a remote location and connected to the scan head via an optical fiber, is used for collection of the filtered signals.

A second side of the scan head may support an LED point scanning system, as disclosed in commonly assigned U.S. patent application Ser. No. 08/438,416 and incorporated herein by reference. The LED light source on this second side of the scan head provides a different stimulating wavelength than does the first side of the compact scan head of the present invention. With this second wavelength, fluorescence and reflective analysis of the target samples may be performed. The LED point scanning is preferably accomplished through the use of a spatial filter with a pinhole aperture, or an optical fiber, in the stimulating light path. The stimulating beam is focused into the pinhole or the fiber. This restriction of the diameter of the stimulating beam provides an apparent point light source and allows for rapid, high resolution scanning.

A support wall preferably separates the first side of the scan head from the second side and provides the physical support for the various elements. Thus, the two sides do not share any optical elements. Within the first side, however, many optical elements are common to both the storage phosphor emission and fluorescence modalities, i.e. the first and second data channels. For example, the laser diode light source and the beam splitter are common to both modalities. The third data channel of the second side of the scan head is physically and optically separate from the first and second data channels.

Although three data channels are particularly advantageous, the compact, movable scan head of the present invention may comprise any two of the above channels. Furthermore, additional channels providing additional stimulating beams may be incorporated into the scan head.

By incorporating the various elements into a compact scan head and moving the scan head, as opposed to moving a scanning mechanism within the optical system, a lightweight, high speed, and extremely versatile scanning system is achieved. The present invention may be used for analysis of storage phosphor screens and samples within membranes, electrophoretic gels, and microtiter sample plates, among others.

BEST MODE FOR CARRYING OUT THE INVENTION

Figure 1:
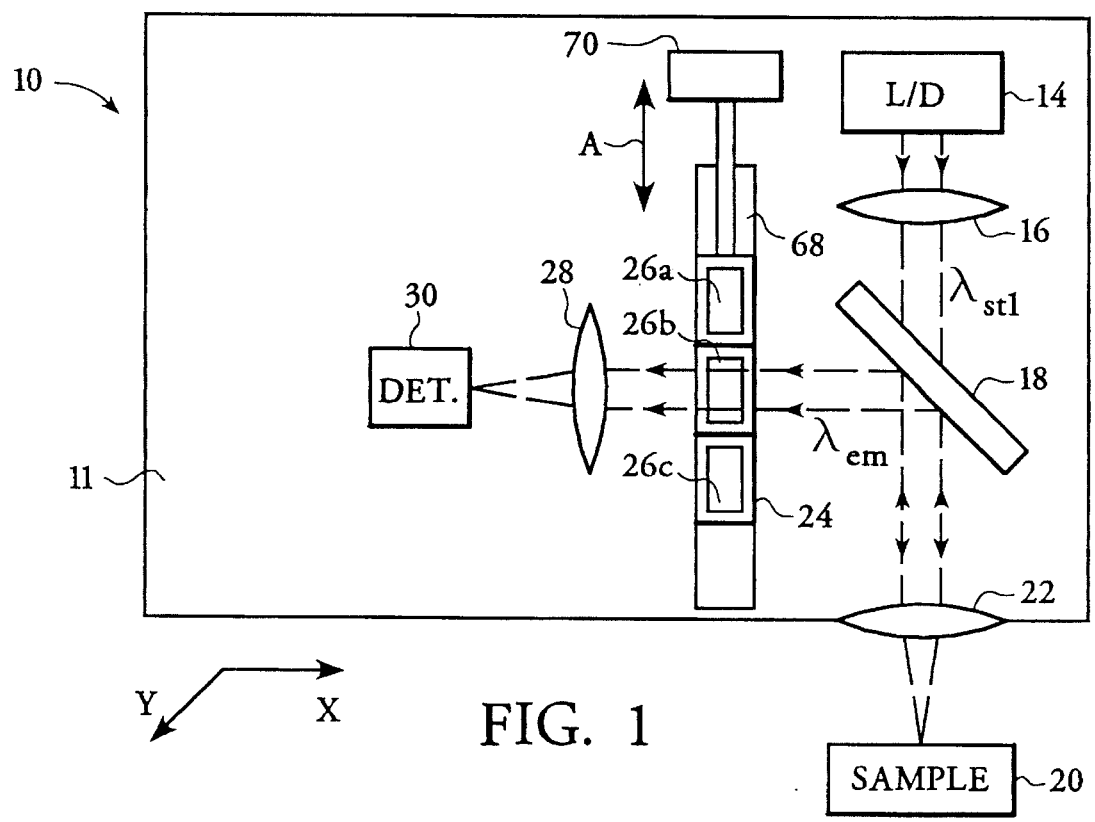
FIG. 1 is a plan view of a first side of the scan head of the present invention, with a laser diode light source.

With reference to FIG. 1, laser diode 14 is shown providing a beam of a first wavelength $\lambda_{st1}$. This exciting or stimulating beam is preferably passed through collimating lens 16 and then passes through beam splitter 18. After passing through beam splitter 18, the stimulating beam of wavelength $\lambda_{st1}$ passes through objective 22 and is focused onto a spot of sample 20 to cause signal radiation to be returned from the sample. The signal radiation emitted from sample 20 is gathered by objective 22, which has a high numerical aperture, into an emission beam and is directed back toward beam splitter 18.

Beam splitter 18 is an interference-type spectral beam splitter designed to pass light of a specific wavelength, for example the laser diode wavelength $\lambda_{st1}$, and to reflect light of a lower or higher wavelength than $\lambda_{st1}$. As stated earlier, "wavelength" includes wavelength bands, as typical emission for certain applications occur over ranges rather than as discrete wavelengths. In FIG. 1, the beam representing the light or signal radiation emitted by the sample has a wavelength of $\lambda_{em}$ and is reflected by beam splitter 18 toward a detection path.

Figure 3:
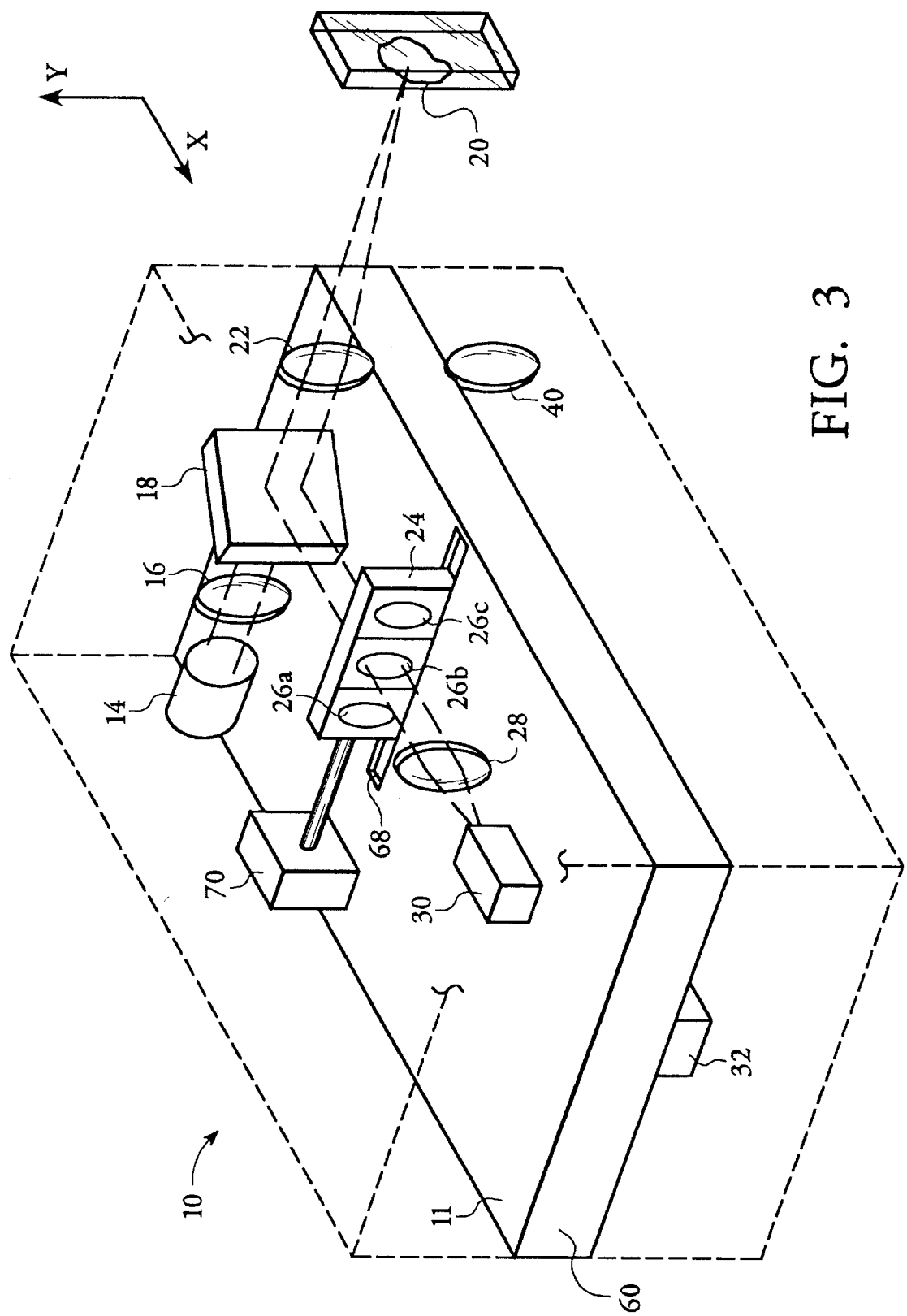
FIG. 3 is a perspective view of the optical elements of FIG. 1 and the support wall of the scan head.

Since the wavelength $\lambda_{em}$ may be of a wavelength lower or higher than the stimulating wavelength $\lambda_{st1}$, a filter system is preferred in the detection path to isolate the desired sample emission for detection. Filter changer assembly 24 is shown in the detection path of FIG. 1, as an example of a filter system useful for isolation of emission. Filter changer assembly 24 contains three filters 26a–c. At least one of these filters isolates a beam of a wavelength $\lambda_{em}$, particularly $\lambda_{em/p}$, which is lower or shorter than $\lambda_{st1}$, and at least one of these filters isolates a beam of wavelength $\lambda_{em}$, particularly $\lambda_{em/f}$ which is higher or longer than wavelength $\lambda_{st1}$. The filter changer assembly may be moved by a shifting means 70, as shown by arrow A. This allows the correct filter to be placed in the path of the emission beam. FIG. 3 shows a means for shifting each of the filters within a slot 68 in support wall 60 of the scan head. The means for shifting 70 may be an actuator driven by a motor. Alternatively, the filter changer assembly 24 may have a plurality of filters in some other configuration, e.g. the filters may be mounted on a wheel and preferably rotated by a motor.

Figure 5:
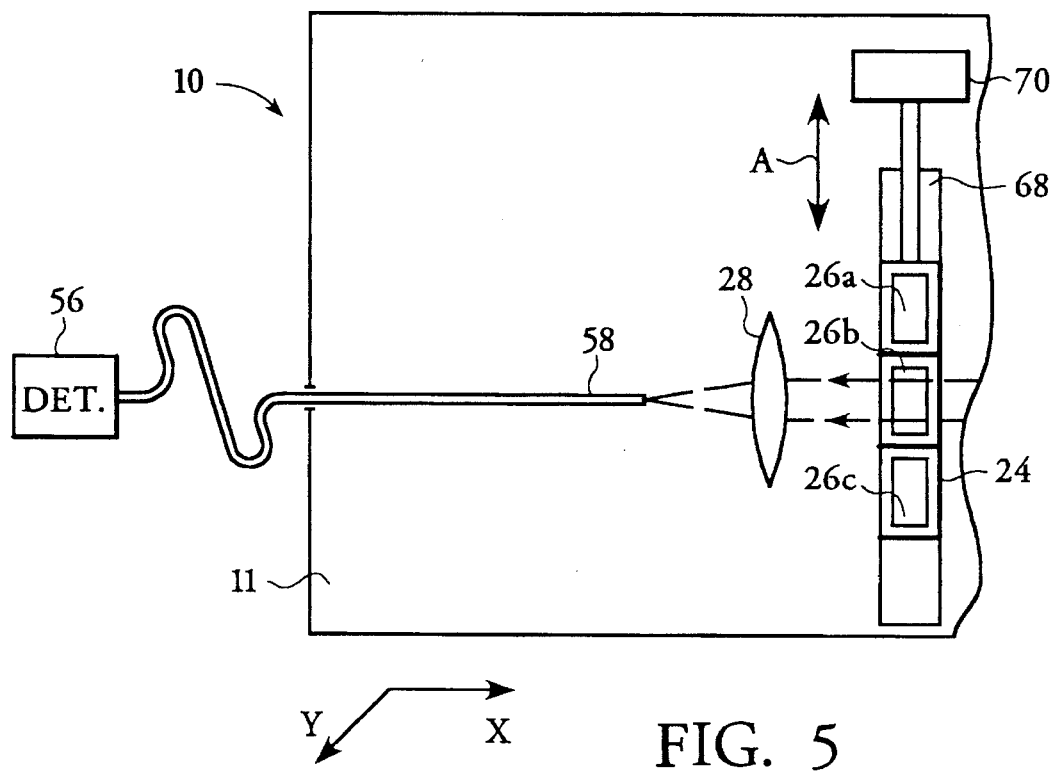
FIG. 5 is a plan view of a portion of FIG. 1, showing an alternate embodiment of the detector placement on the first side of the scan head.

The filtered emission are then passed through focusing lens 28 and onto the detector 30. The detector may be mounted on the scan head, as shown by detector 30 of FIG. 1, or it may be positioned remotely, as shown in FIG. 5. In this latter case, the focusing lens 28 focuses the emission beam into an optical fiber 58 which transmits the emission beam to the remotely positioned detector 56.

The laser diode or other compact laser device may be of any of a variety of colors and wavelengths. For example, infrared and red laser diodes are available. The laser may also be a compact, solid state, frequency-doubled diode or frequency-doubled diode pumped YAG laser. The use of a red laser diode is particularly useful, as it provides a stimulating beam having a wavelength $\lambda_{st1}$ of approximately 635 nm. Stimulation of the sample with light of this wavelength may cause fluorescence emission of a higher wavelength, e.g. 650 to 700 nm, and emission from a storage phosphor screen at a lower wavelength, e.g. approximately 390 nm. Thus, beam splitter 18 passes light of 635 nm but reflects both lower and higher numbers or shorter and longer wavelengths. "Approximately," as used here, indicates a value within ±10% of the given value.

The first side 11 of scan head 10 thus shows a first data channel, capable of reading storage phosphor screens by stimulating with wavelength $\lambda_{st1}$ and detecting emission through use of the appropriate filter in the detection path, and a second data channel, capable of reading fluorescent emission by stimulating with wavelength $\lambda_{st1}$ and detecting emission through use of the appropriate filter in the detection path. The first channel detects emission of wavelength $\lambda_{em/p}$ where $\lambda_{em/p} < \lambda_{st1}$. The second channel detects emission of wavelength $\lambda_{em/f}$ where $\lambda_{em/f} > \lambda_{st1}$. Collection and detection of transmitted and reflected signals resulting from laser diode stimulation may also be achieved, as through transmission collection and detection device 78, shown in FIG. 7, or through other well-known detection paths.

Figure 4:
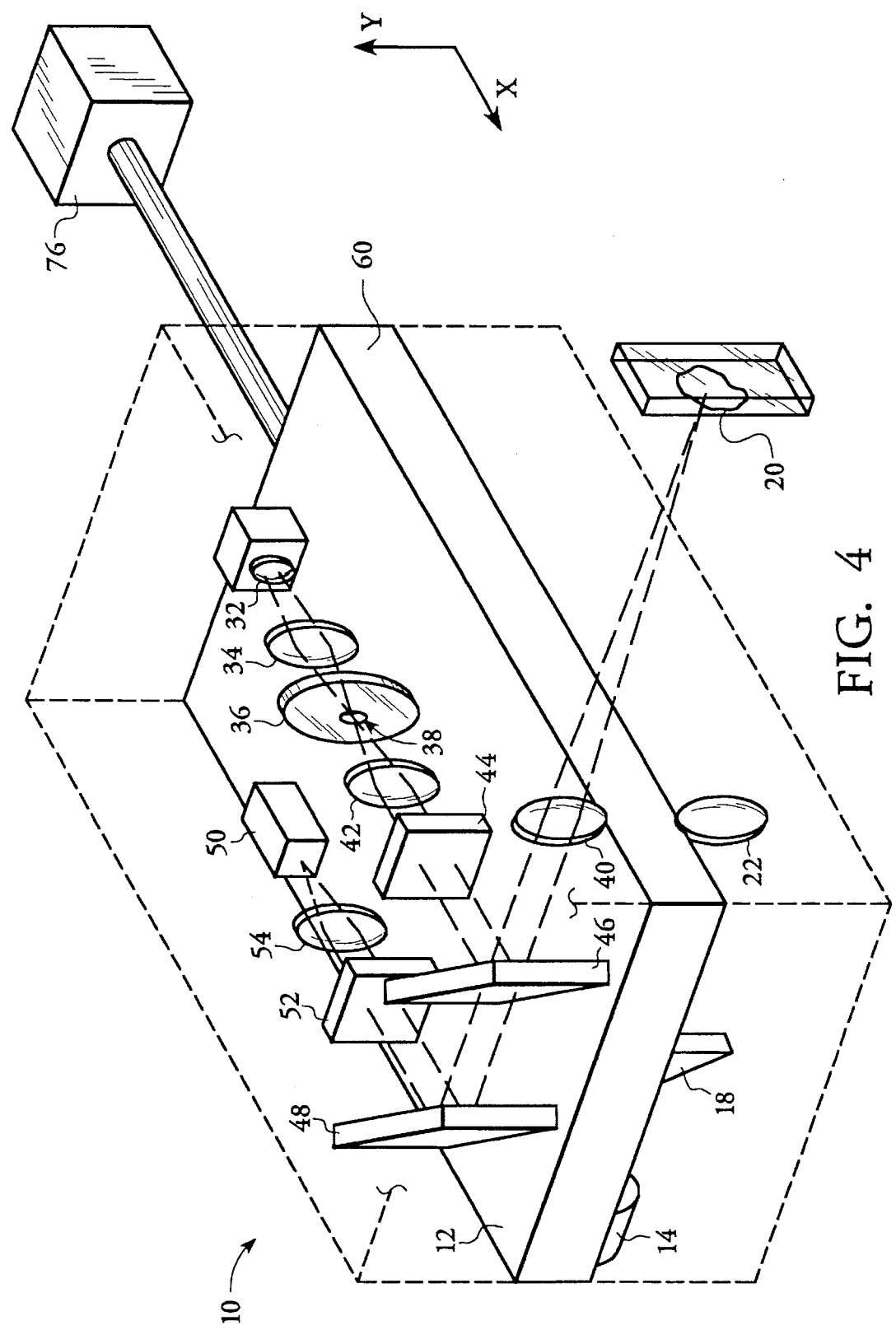
FIG. 4 is a perspective view of the optical elements of FIG. 2 and a second side of the support wall of the scan head.

Compact scan head 10 may be moved across a sample in two dimensions, as seen by arrows X and Y, which represent perpendicular axes. Alternatively, scan head 10 may move in a first direction relative to sample 20 and the sample may be moved in a perpendicular direction as by a motorized stage, or the scanning may occur according to some other scan pattern. The scan head may be moved by sliding it along a rail with a belt and pulley, lead screw, or other actuating means. FIG. 4 shows a means for moving 76 the scan head. Scanning is preferably accomplished in a point-by-point imaging manner wherein a plurality of spots of the sample are sequentially subjected to stimulation and detection of resulting emission.

Figure 2:
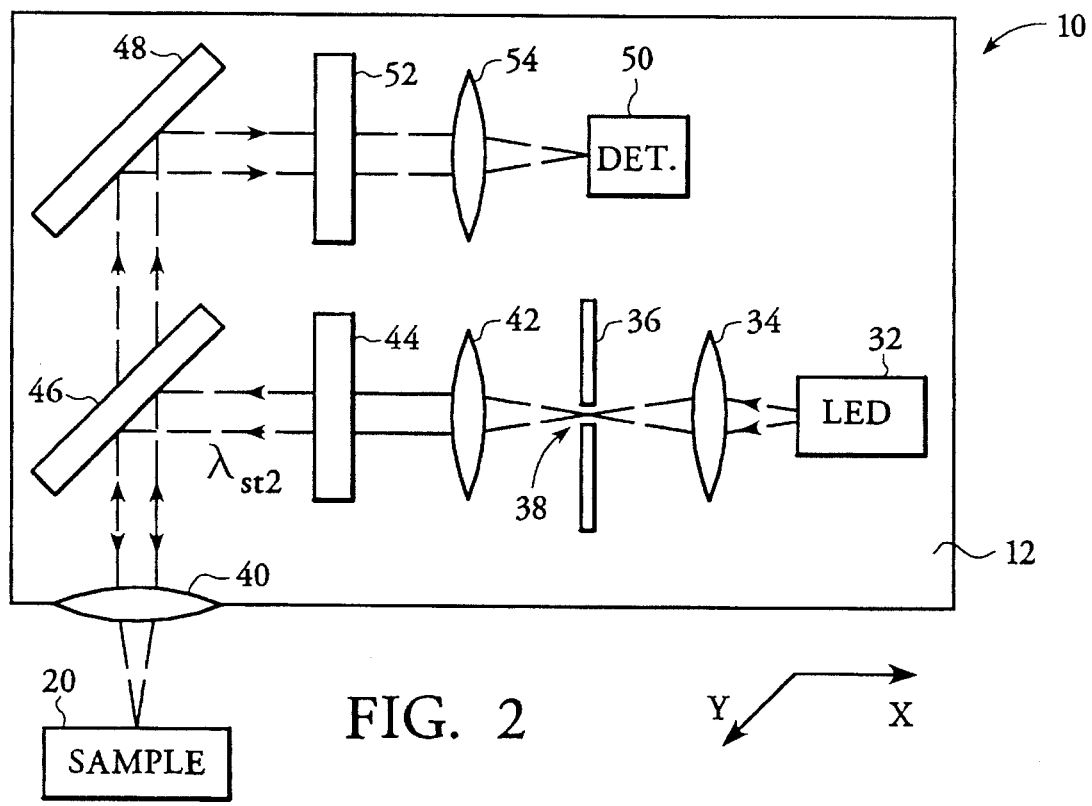
FIG. 2 is a plan view of a second side of the scan head of the present invention, with an LED light source.

FIG. 2 shows a second side 12 of scan head 10 of the present invention. The second side supports an LED point scanning system, such as that disclosed in commonly assigned patent application U.S. Ser. No. 08/438,416. As seen in FIG. 2, LED 32 provides a stimulating beam of a second wavelength $\lambda_{st2}$ which is focused by focusing lens 34 into the pinhole aperture 38 of spatial filter 36. This effectively restricts the diameter of the stimulating beam and defines the necessary resolution for stimulation. The stimulating beam of wavelength $\lambda_{st2}$ thus functions as a point light source. This is an important advantage as an LED is an incoherent light source and restriction of this nature allows for high resolution scanning. Alternatively, an optical fiber may provide the necessary restriction of the stimulation beam.

Figure 7:
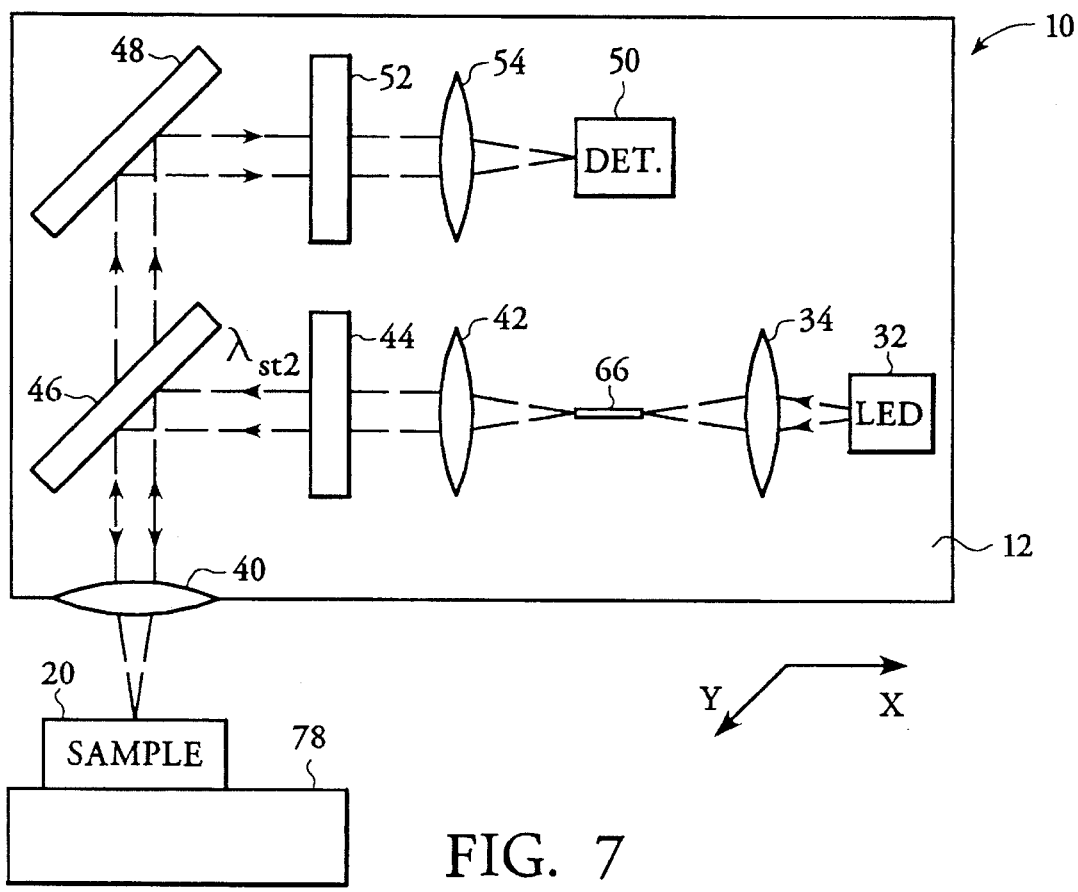
FIG. 7 is a plan view of an alternate embodiment of the stimulating beam restriction of the second side of the scan head.

FIG. 7 shows this alternate embodiment wherein an optical fiber 66 replaces spatial filter 36; focusing lens 34 then serves to focus the stimulating beam of wavelength $\lambda_{st2}$ into optical fiber 66. The focal points of lenses 34 and 42 are also spaced apart with fiber 66 between them. FIG. 7 also shows a transmitted light collector and detector 78. This transmission system 78, although shown in the FIG. 7 embodiment for clarity, may be used with any of the light sources on either side of the scan head.

Figure 6:
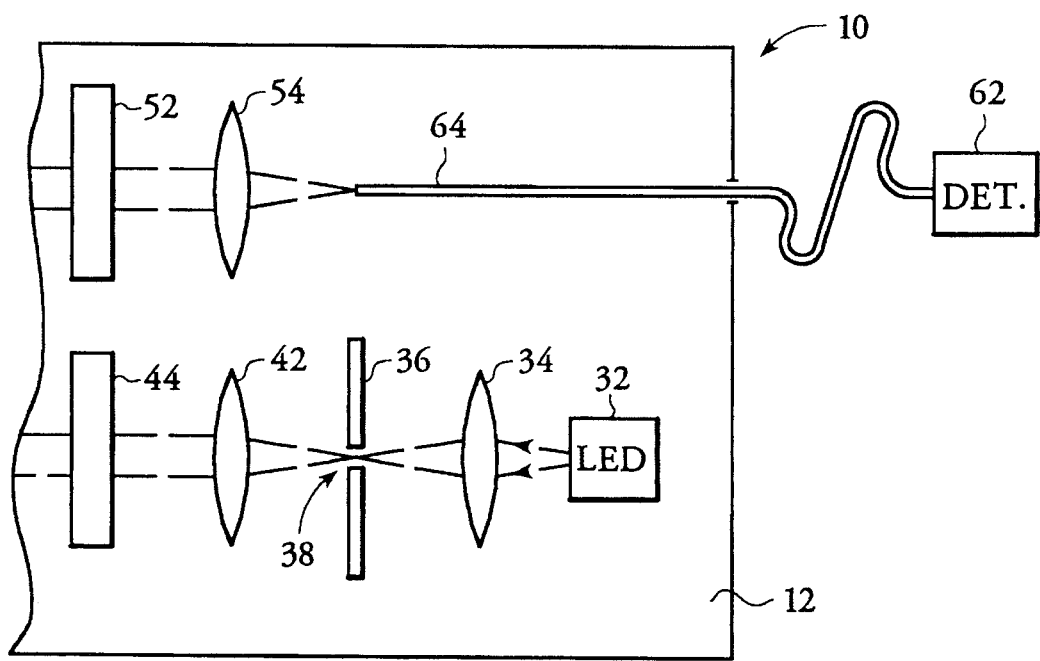
FIG. 6 is a plan view of a portion of FIG. 2, showing an alternate embodiment of the detector placement on the second side of the scan head.

The restricted stimulating beam is collected by collimating lens 42 and passed through a filter 44 and then directed onto the sample. FIG. 2 shows a beam splitter 46 reflecting the stimulating beam and directing it toward objective 40 where it is focused onto a spot of sample 20. Light emitted or returned from the sample, for example fluorescent or reflective signal radiation, is then collected by objective 40 and passes through beam splitter 46 to be directed toward the detection path of this third data channel. An appropriate beam splitter for fluorescent or reflective emission may be used. The emission returned from the sample are reflected by mirror 48 in FIG. 2 and directed through a second filter 52 and then through a second focusing lens 54. Focusing lens 54 serves to focus the beam onto detector 50. As in FIG. 1, the detector may be mounted on the scan head 10 or it may be positioned remotely and connected to the scan head via an optical fiber. FIG. 6 shows this detector placement alternative, with focusing lens 54 serving to focus the returned emission into optical fiber 64 for transmission to detector 62, which is off scan head 10.

As disclosed in U.S. Ser. No. 08/438,416, other variations of the LED point scanning system are possible on this second side of the compact scan head of the present invention. The LED provides an inexpensive alternative to the laser diode and is particularly useful for certain specified wavelengths. For example, a blue LED providing a stimulation beam at a wavelength centered at approximately 450 nm may advantageously be used to stimulate samples for chemi-fluorescence applications. Green, yellow, orange, red, and infrared LEDs are also available.

FIGS. 3 and 4 illustrate the described two sides of the scan head in perspective. FIGS. 3 and 4 depict support wall 60, which is a preferred support within scan head 10, and serves as the support to which the optical elements of all configurations are mounted.

The compact scan head of the present invention contains multiple scanning modalities which may or may not be coincident. For example, in FIGS. 3 and 4, two objectives 22 and 40 are visible. Objective 22 is part of the laser diode optical system on the first side 11 of the scan head, and objective 40 is part of the LED point scanning system of the second side 12 of the scan head. Support wall 60 completely separates all of the optical elements of the two sides of the scan head and, thus, the laser diode and the LED optical systems are separate. The first and second data channels share a laser diode, a collimating lens, beam splitter, and a detector, among other optical elements, however, and so, these modalities are at least partially coincident. The sample may be mounted relative to the scan head so that scanning by either side, and thus either optical configuration, or according to any of the three channels of the scan head, is possible. This is facilitated by the movable scan head and its preferred two-dimensional translation relative to the sample.

Figure 8:
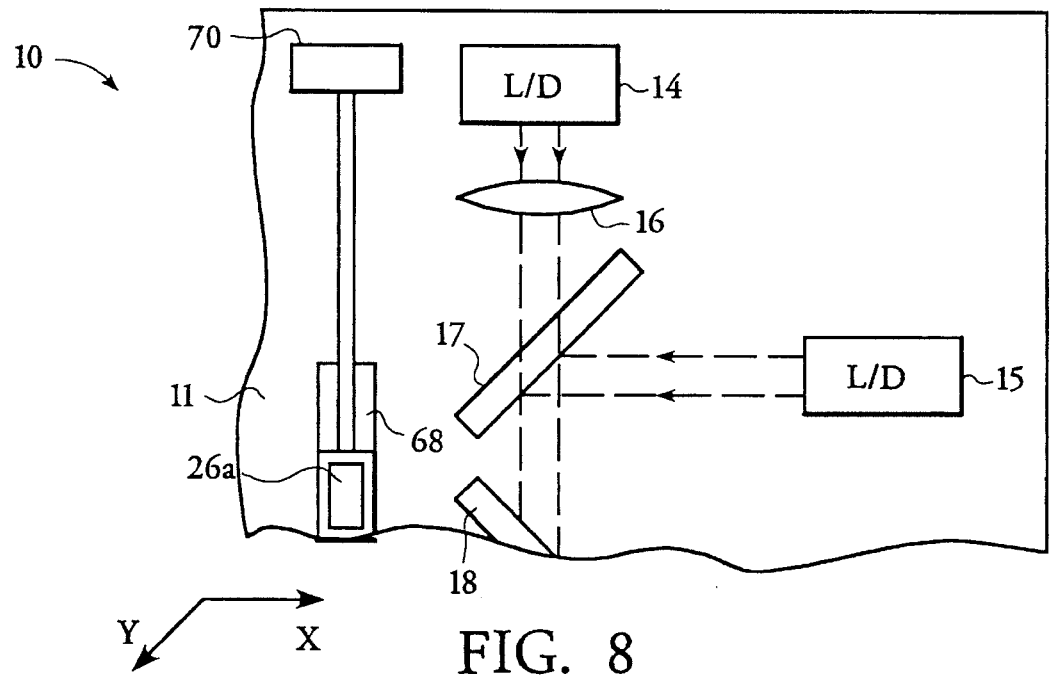
FIG. 8 is a portion of a plan view of an alternate embodiment of the scan head, showing multiple stimulating beams on a single side of the scan head.

FIG. 8 shows an alternate embodiment of the scan head, with multiple stimulating beams. On the first side 11 of the scan head, a second laser diode 15 is shown. Laser diode 15 provides a stimulating beam which may be included in the stimulation optical path of the first side of the scan head via beam splitter 17. This second source may provide a different stimulating wavelength than the first source. Alternatively, the second source may provide a different optical property than the first source. For example, the two sources may provide pulsed and continuous wave beams, or polarized and nonpolarized beams. In this manner, a plurality of light sources may be used on the first side of the scan head. Stimulation preferably occurs in a sequential manner. The second side of the scan head may also have more than one light source. A second LED with an affiliated beam restriction means may be inserted into the optical path of the second side of the scan head, for example. These multiple sources on the second side may also provide unique wavelengths or other properties. The various channels on opposite sides of the scan head may also utilize beams of different optical properties, in general, rather than simply utilizing different wavelengths for stimulation.

Figure 9:
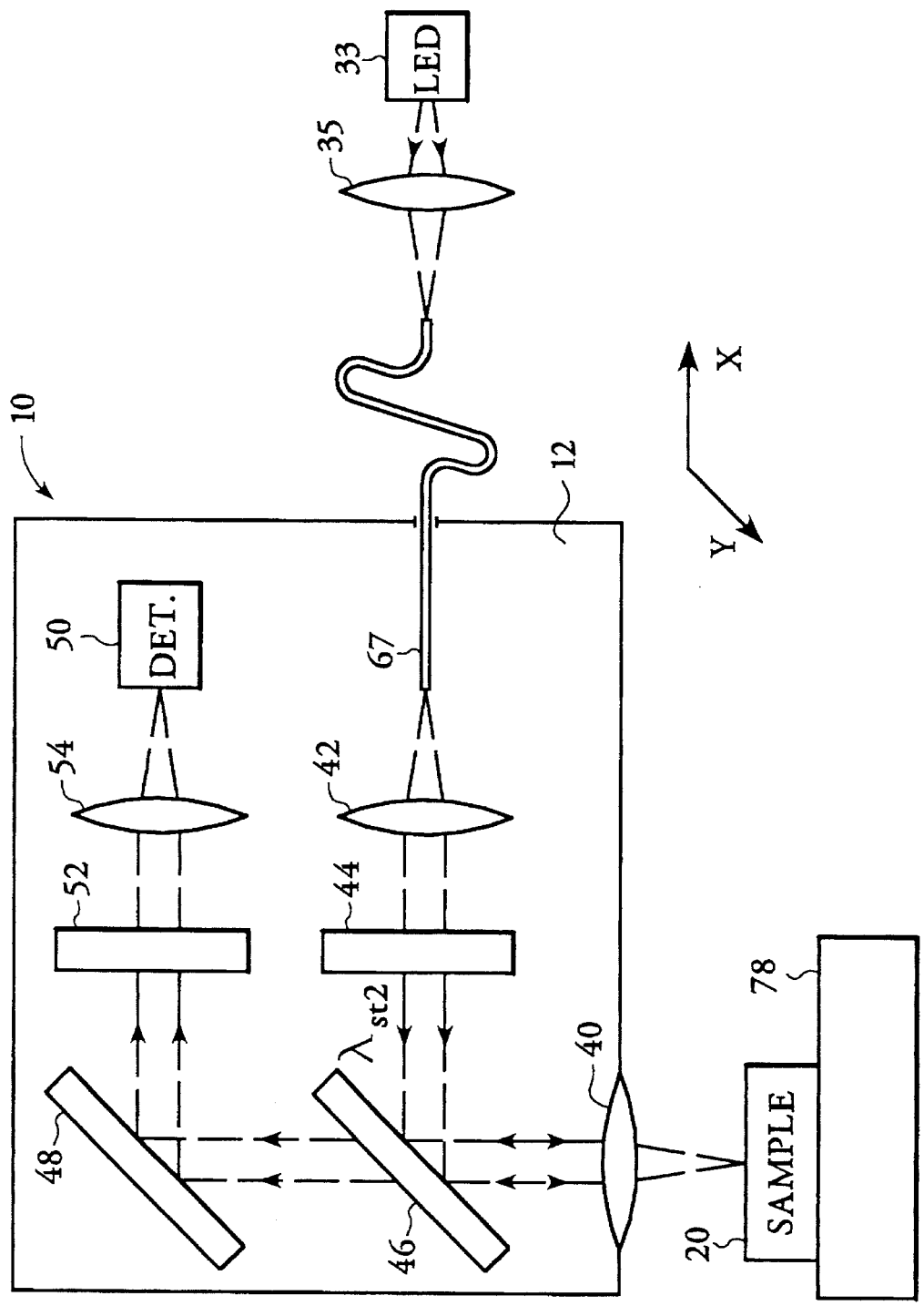
FIG. 9 is a plan view of an alternate embodiment of the scan head, showing optical fiber delivery of a stimulating beam to the scan head from a remotely positioned light source.

With reference to FIG. 9, optical fiber delivery via optical fiber 67, from remotely positioned LED 33 to the scan head is shown. LED 33 provides a stimulating beam which is focused by lens 35 into fiber 67. Fiber 67, in this instance, serves as both a delivery means and a restriction means. The restricted beam is received by lens 42, as before, and directed toward the sample. The laser diode stimulating beam of the first side may also be delivered from a remotely positioned source to the scan head through the use of an optical fiber.

Although separate on-head detectors 30 and 50, seen in FIGS. 1–2, and off-head detectors 56 and 62, seen in FIGS. 5–6, are shown and described for the laser diode and LED optical systems, a combined detector may be used for the various channels and systems. A single detector may be particularly convenient when positioned remotely and connected to relevant locations within the scan head 10 by optical fibers. An array-type detector may also be used for the various channels. Additionally, a spatial filter may be added to the detection path of the laser diode or LED optical systems, limiting the signals reaching the detector and, in certain cases, creating confocal systems.

Figure 10:
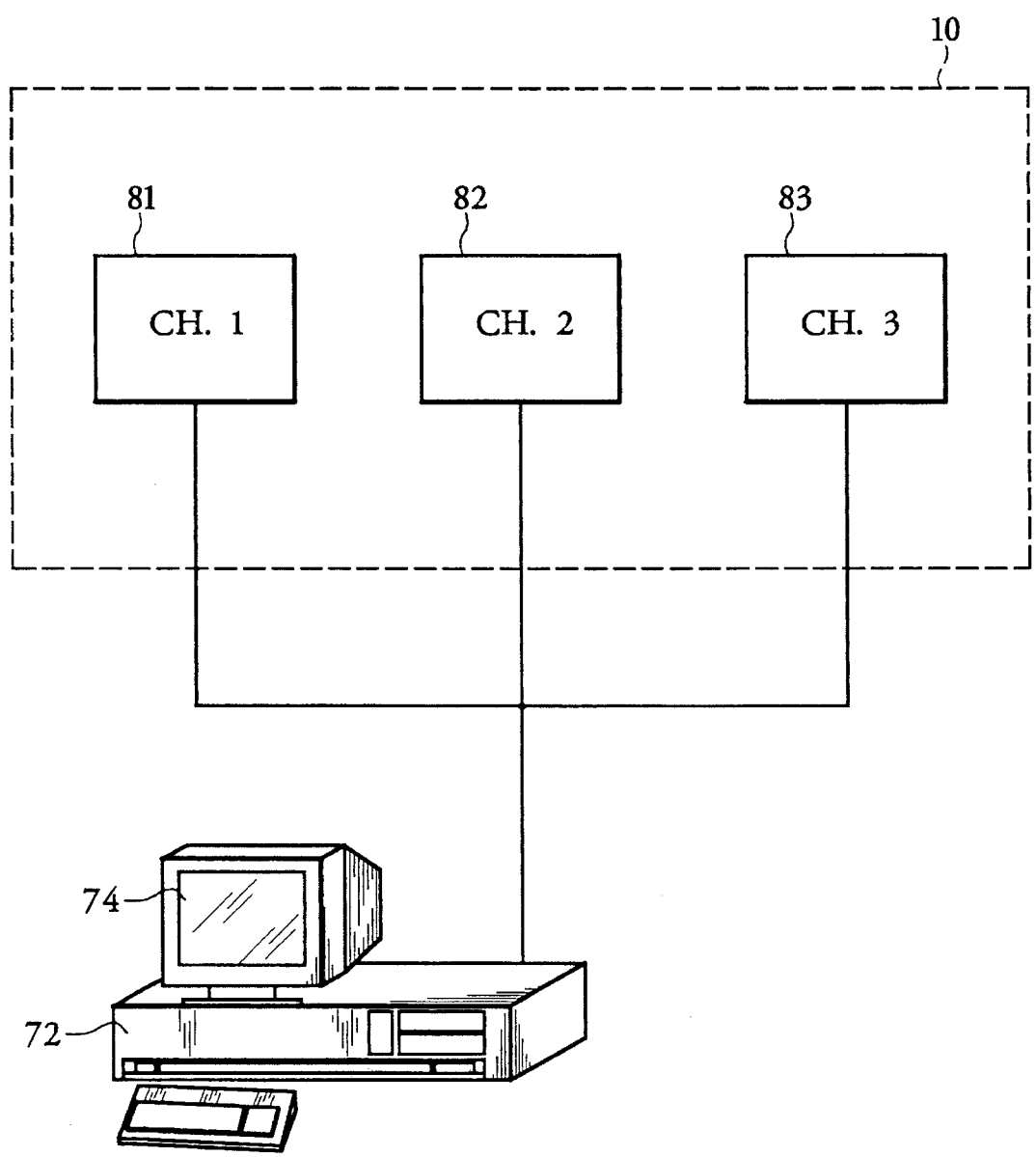
FIG. 10 is a plan view of a data collection and display apparatus for use with the scan head of the present invention.

Each of the three channels, 81, 82, and 83 of FIG. 10, provides data regarding emission within the channel. These data are collected from the various detectors by a data analysis or processing means 72, such as a computer, and displayed, such as on a multi-channel data display 74, or saved in a memory for future analysis. The video monitor, or other display, may display data from any or all of the three channels. Multi-channel displays are known in the art. The data analysis means may be programmed to operate the channels sequentially on the sample or to direct operation of the appropriate channel according to the nature of the sample. For example, the particular dimensions of a storage phosphor screen or of a microtiter plate may cause first or third data channel stimulation and detection of emission to occur, the fitting of the sample holder onto the stage triggering the appropriate channel. Simultaneous reading of a sample according to more than one channel may also occur.

The compactness of the scan head allows for high speed scanning and its optical systems allow for high resolution scanning. In addition, the scan head of the present invention provides versatility with regard to sample formats and types of optical analysis, thus contributing to reduced laboratory operating costs.

We claim:

1. A movable scan head with multiple scanning modalities for analyzing a sample, the scan head comprising:
   (a) first channel means for stimulating the sample with a beam of a first wavelength and detecting resultant storage phosphor emission from the sample,
   (b) second channel means for stimulating the sample with a beam of the first wavelength and detecting resultant fluorescent emission from the sample,
   (c) third channel means for stimulating the sample with a beam of a second wavelength and detecting resultant second wavelength-stimulated emission from the sample,
   (d) means for moving the scan head relative to the sample in a scan pattern, and
   (e) analysis means for collecting information regarding emission from the first, second, and third channel means.

2. The scan head of claim 1 further comprising:
   means for displaying the information regarding emission from any of the first, second, and third channel means.

3. The scan head of claim 1 wherein the third channel means is separated from both the first channel means and the second channel means.

4. The scan head of claim 1 wherein the first channel means and second channel means have common portions of their respective optical paths.

5. The scan head of claim 1 wherein the first and second channel means are positioned on a first side of a support wall of the scan head and the third channel means is positioned on a second side of the support wall.

6. The scan head of claim 1 wherein the first and second channel means include a compact, lightweight laser device.

7. The scan head of claim 6 wherein the first and second channel means include a laser diode.

8. The scan head of claim 1 wherein the first and second channel means include a beam splitter for passing the first wavelength stimulating beam and for reflecting emission received from the sample which is of a wavelength lower than or higher than the first wavelength.

9. The scan head of claim 8 wherein the first and second channel means include a filter changer assembly disposed to receive emission reflected by the beam splitter, the filter changer assembly having at least one filter for passing emission received from the sample which is of a wavelength lower than the first wavelength and at least one filter for passing emission received from the sample which is of a wavelength higher than the first wavelength, and having means for shifting each of the filters into the first and second channel means.

10. The scan head of claim 1 wherein the third channel means includes an LED.

11. The scan head of claim 1 wherein the third channel means includes a spatial filter having a pinhole aperture and a means for focusing the second wavelength stimulating beam into the pinhole aperture for restriction of the diameter of the second wavelength stimulating beam to a point light source for stimulation of the sample.

12. The scan head of claim 1 wherein the third channel means includes an optical fiber and a means for focusing the second wavelength stimulating beam into an optical fiber for restriction of the diameter of the second wavelength stimulating beam to a point light source for stimulation of the sample.

13. The scan head of claim 1 wherein the analysis means directs operation of the first, second, and third channel means sequentially on the sample.

14. The scan head of claim 1 further comprising:
   a fourth channel means for stimulating the sample with a beam of a third wavelength and detecting resultant third wavelength stimulated emission from the sample,
   wherein the analysis means for collecting information regarding emission from the first, second, and third channel means collects information regarding emission from the fourth channel means.

15. The scan head of claim 1 further comprising a fifth channel means for stimulating light with a beam of a fourth wavelength and detecting resultant fourth wavelength-stimulated emission from the sample,
   wherein the analysis means for collecting information regarding emission from the first, second, and third channel means collects information regarding emission from the fifth channel means.

16. A movable scan head with multiple scanning modalities for analyzing a sample, the scan head comprising:
   (a) first channel means for stimulating the sample with a beam of a first wavelength and detecting resultant storage phosphor emission from the sample,
   (b) third channel means for stimulating the sample with a beam of a second wavelength and detecting resultant second wavelength-stimulated emission from the sample,
   (c) means for moving the scan head relative to the sample in a scan pattern, and
   (d) analysis means for collecting information regarding emission from the first and third channel means.

17. A movable scan head with multiple scanning modalities for analyzing a sample, the scan head comprising:
   (a) first channel means for stimulating the sample with a beam of a first wavelength and detecting resultant storage phosphor emission from the sample,
   (b) second channel means for stimulating the sample with a beam of the first wavelength and detecting resultant fluorescent emission from the sample,
   (c) means for moving the scan head relative to the sample in a scan pattern, and
   (d) analysis means for collecting information regarding emission from the first and second channel means.

18. A movable scan head with multiple scanning modalities for analyzing a sample, the scan head comprising:
   (a) second channel means for stimulating the sample with a beam of a first wavelength and detecting resultant fluorescent emission from the sample,
   (b) third channel means for stimulating the sample with a beam of a second wavelength and detecting resultant second wavelength-stimulated emission from the sample,
   (c) means for moving the scan head relative to the sample in a scan pattern, and
   (d) analysis means for collecting information regarding emission from the second and third channel means.

19. A movable scan head with three data channels for variable optical analysis of samples, the scan head comprising:

a first data channel having a laser diode providing a stimulating beam of a first stimulating wavelength $\lambda_{st1}$, and a first detection path for isolating emission and for providing related data for emission from the sample of a wavelength $\lambda_{em/p}$ where $\lambda_{em/p}<\lambda_{st1}$, a second data channel utilizing the laser diode of the first data channel to provide a stimulating beam of the first stimulating wavelength $\lambda_{st1}$, and having a second detection path for isolating emission and for providing related data for emission from the sample of a wavelength $\lambda_{em/f}$ where $\lambda_{em/f}>\lambda_{st1}$, a third data channel having an LED providing a stimulating beam of a second stimulating wavelength $\lambda_{st2}$, a means for restricting the diameter of the stimulating beam of wavelength $\lambda_{st2}$, a means for directing the restricted stimulating beam of wavelength $\lambda_{st2}$ onto the sample, and a third detection path for isolating emission and for providing related data for LED-stimulated emission from the sample, means for moving the scan head relative to the sample along a first axis, and data processing means for collecting the data regarding sample emission from the first, second, and third data channels.

20. The scan head of claim 19 further comprising:
means for displaying the data from any of the first, second, and third data channels.

21. The scan head of claim 19 further comprising:
means for moving the scan head relative to the sample along a second axis, the second axis being perpendicular to the first axis.

22. The scan head of claim 19 wherein the first and second data channels are mounted on a first side of a support wall of the scan head and the third data channel is mounted on a second side of the support wall of the scan head.

23. The scan head of claim 19 wherein the first and second data channels are at least partially coincident.

24. The scan head of claim 19 wherein the first and second data channels share a collimating lens for collimating the stimulating beam of wavelength $\lambda_{st1}$.

25. The scan head of claim 19 wherein the first and second data channels share an objective for focusing the stimulating beam of wavelength $\lambda_{st1}$ onto a spot of the sample and for collecting the resulting emission from the sample.

26. The scan head of claim 19 wherein the first and second data channels share a beam splitter, the beam splitter passing the stimulating beam of wavelength $\lambda_{st1}$ and reflecting emission of wavelengths $\lambda_{em/p}$ and $\lambda_{em/f}$.

27. The scan head of claim 26 wherein the first and second detection paths share a filter changer assembly, the filter changer assembly having a plurality of filters and a means for shifting each of the filters into the first and second detection paths, at least one filter for isolating emission of wavelength $\lambda_{em/p}$, and at least one filter for isolating emission of wavelength $\lambda_{em/f}$, the filter changer assembly disposed to receive the emission reflected by the beam splitter.

28. The scan head of claim 27 wherein the first and second detection paths share a laser diode detection path focusing lens for receiving the isolated emission from the filter changer assembly and for focusing the isolated emission onto a laser diode scan-head mounted detector.

29. The scan head of claim 27 wherein the first and second detection paths share a laser diode detection path focusing lens and a laser diode detection path optical fiber, the laser diode detection path focusing lens for receiving the isolated emission from the filter changer assembly and for focusing the isolated emission into the laser diode detection path optical fiber, the laser diode detection path optical fiber transmitting the isolated emission to a laser diode remotely positioned stationary detector.

30. The scan head of claim 19 wherein the laser diode provides a red stimulating beam.

31. The scan head of claim 30 wherein the wavelength $\lambda_{st1}$ is approximately 635 nm.

32. The scan head of claim 19 wherein the emission from the sample of wavelength $\lambda_{em/p}$ comprise storage phosphor emission.

33. The scan head of claim 19 wherein the emission from the sample of wavelength $\lambda_{em/f}$ comprise fluorescent emission.

34. The scan head of claim 19 wherein the means for restricting the diameter of the stimulating beam of wavelength $\lambda_{st2}$ comprises a spatial filter with a pinhole aperture, and an LED stimulation path focusing lens for focusing the stimulating beam of wavelength $\lambda_{st2}$ into the pinhole aperture.

35. The scan head of claim 19 wherein the means for restricting the diameter of the stimulating beam of wavelength $\lambda_{st2}$ comprises an LED stimulation path optical fiber and an LED stimulation path focusing lens for focusing the stimulating beam of wavelength $\lambda_{st2}$ into the LED stimulation path optical fiber.

36. The scan head of claim 19 wherein the third detection path includes an LED detection path focusing lens for receiving the LED-stimulated emission and for focusing the LED-stimulated emission onto an LED scan-head mounted detector.

37. The scan head of claim 19 wherein the third detection path includes an LED detection path focusing lens and an LED detection path optical fiber, the LED detection path focusing lens focusing the LED-stimulated emission into the LED detection path optical fiber, the LED detection path optical fiber transmitting the LED-stimulated emission from the scan head to an LED remotely positioned stationary detector.

38. The scan head of claim 19 wherein the wavelength $\lambda_{st2}$ is approximately 450 nm.

39. A movable scan head for sample analysis via multiple scanning modalities, the scan head comprising:

(a) a first side supporting a laser diode optical system including:
  (i) a laser diode stimulating beam of a wavelength $\lambda_{st1}$,
  (ii) an objective for focusing the laser diode stimulating beam of wavelength $\lambda_{st1}$ onto a first spot of the sample to cause signal radiation to be returned from the sample, and for collecting the returned signal radiation to form an emission beam of a wavelength $\lambda_{em}$,
  (iii) a beam splitter for passing the stimulating beam of wavelength $\lambda_{st1}$ and for reflecting the emission beam of wavelength $\lambda_{em}$,
  (iv) a filter changer assembly having a plurality of filters, at least one filter for passing the emission beam of wavelength $\lambda_{em}$ when $\lambda_{em}>\lambda_{st1}$, and at least one filter for passing the emission beam of wavelength $\lambda_{em}$ when $\lambda_{em}<\lambda_{st1}$, and having a means for shifting the filters as needed into the emission beam path, the filter changer assembly disposed to receive the emission beam reflected by the beam splitter, and
  (v) means for receiving and detecting the filtered emission beam of wavelength $\lambda_{em}$, (b) a second side supporting an LED optical system including:

(i) an LED stimulating beam of a wavelength $\lambda_{st2}$, (ii) means for restricting the diameter of the LED stimulating beam of wavelength $\lambda_{st2}$ for point scanning of the sample, (iii) means for receiving the restricted LED stimulating beam of wavelength $\lambda_{st2}$ and for directing the restricted LED stimulating beam of wavelength $\lambda_{st2}$ onto a second spot of the sample to cause signal radiation to be returned from the sample, and (iv) means for collecting and detecting the signal radiation returned from the sample, (c) means for moving the scan head relative to the sample to stimulate a plurality of spots on the sample in a scan pattern, and (d) data processing means for collecting data regarding the signal radiation returned from the sample of the laser diode and LED optical systems.

40. The scan head of claim 39 further comprising:

means for displaying the data from the laser diode and LED optical systems.

41. The scan head of claim 39 wherein the means for restricting the diameter of the LED stimulating beam of wavelength $\lambda_{st2}$ comprises a spatial filter with a pinhole aperture, and a focusing lens for focusing the LED stimulating beam of wavelength $\lambda_{st2}$ into the pinhole aperture.

42. The scan head of claim 39 wherein the means for restricting the diameter of the LED stimulating beam of wavelength $\lambda_{st2}$ comprises an LED restriction optical fiber and a focusing lens for focusing the LED stimulating beam of wavelength $\lambda_{st2}$ into the LED restriction optical fiber.

43. The scan head of claim 39 wherein the laser diode stimulating beam of wavelength $\lambda_{st1}$ is provided by a laser diode source supported on the first side of the scan head.

44. The scan head of claim 39 wherein the laser diode stimulating beam of wavelength $\lambda_{st1}$ is provided by a laser diode delivery optical fiber from a remotely positioned laser diode source.

45. The scan head of claim 39 wherein the LED stimulating beam of wavelength $\lambda_{st2}$ is provided by an LED source supported on the second side of the scan head.

46. The scan head of claim 39 wherein the LED stimulating beam of wavelength $\lambda_{st2}$ is provided by an LED delivery optical fiber from a remotely positioned laser diode source.

47. A movable scan head for sample analysis via multiple scanning modalities, the scan head comprising:

(a) a first side supporting a laser diode optical system including:

(i) a laser diode stimulating beam of a wavelength $\lambda_{st1}$, (ii) an objective for focusing the laser diode stimulating beam of wavelength $\lambda_{st1}$ onto a first spot of the sample to cause signal radiation to be transmitted through the sample, (iii) means for collecting and detecting the laser diode source transmitted signal radiation from the sample, (b) a second side supporting an LED optical system including:

(i) an LED stimulating beam of a wavelength $\lambda_{st2}$, (ii) means for restricting the diameter of the LED stimulating beam of wavelength $\lambda_{st2}$ for point scanning of the sample, (iii) means for receiving the restricted LED stimulating beam of wavelength $\lambda_{st2}$ and for directing the restricted LED stimulating beam of wavelength $\lambda_{st2}$ onto a second spot of the sample to cause signal radiation to be transmitted through the sample, and (iv) means for collecting and detecting the LED source transmitted signal radiation from the sample, (c) means for moving the scan head relative to the sample to stimulate a plurality of spots on the sample in a scan pattern, and (d) data processing means for collecting data regarding the signal radiation transmitted through the sample of the laser diode and LED optical systems.

48. The scan head of claim 47 further comprising:

means for displaying the data from the laser diode and LED optical systems.

49. A movable scan head with multiple scanning modalities for analyzing a sample, the scan head comprising:

first channel means for stimulating the sample with a beam of a first optical property and detecting resultant emission, second channel means for stimulating the sample with a beam of a second optical property and detecting resultant emission, means for moving the scan head relative to the sample in a scan pattern, and analysis means for collecting information regarding emission from the first and second channel means.

* * * * *